(12) United States Patent
Chen et al.

(10) Patent No.: US 12,419,685 B2
(45) Date of Patent: Sep. 23, 2025

(54) MULTI-WAVELENGTH LASER DEVICE FOR PHOTOCOAGULATION SURGERY

(71) Applicant: National Yang Ming Chiao Tung University, Hsinchu (TW)

(72) Inventors: Yung-Fu Chen, Hsinchu (TW); Hsing-Chih Liang, Hsinchu (TW); Chia-Han Tsou, Hsinchu (TW)

(73) Assignee: National Yang Ming Chiao Tung University, Hsinchu (TW)

( * ) Notice: Subject to any disclaimer, the term of this patent is extended or adjusted under 35 U.S.C. 154(b) by 413 days.

(21) Appl. No.: 18/107,993

(22) Filed: Feb. 9, 2023

(65) Prior Publication Data

US 2024/0108409 A1 Apr. 4, 2024

(51) Int. Cl.
*A61B 18/22* (2006.01)
*A61B 18/00* (2006.01)
*A61B 18/20* (2006.01)

(52) U.S. Cl.
CPC .... *A61B 18/22* (2013.01); *A61B 2018/00589* (2013.01); *A61B 2018/2065* (2013.01); *A61B 2018/208* (2013.01); *A61B 2018/2272* (2013.01)

(58) Field of Classification Search
CPC .......... A61B 18/22; A61B 2018/00589; A61B 2018/2065; A61B 2018/208; A61B 2018/2255; A61B 2018/2272; A61F 2009/00863; A61F 9/00821; A61F 9/00823
See application file for complete search history.

(56) References Cited

U.S. PATENT DOCUMENTS

2007/0230520 A1* 10/2007 Mordaunt ............... A61F 9/008
359/227

* cited by examiner

*Primary Examiner* — Scott Luan
(74) *Attorney, Agent, or Firm* — Tarter Krinsky & Drogin LLP

(57) ABSTRACT

A laser device for photocoagulation surgery is disclosed, wherein the laser device includes a multi-wavelength laser source having a first direction and a second direction different from the first direction. The laser device includes a positioning light source, a first laser light source, a first lens, a second laser light source, a second lens, a third laser light source, a third lens, a fourth laser light source and a fourth lens. The positioning light source configured to project a positioning visible light along the first direction, wherein the positioning visible light has a specific wavelength being about 635 nm. The first laser light source configured to project a first laser light having a first wavelength along the second direction. The first lens disposed in a main optical path of the positioning visible light, and configured to receive the first laser light and reflect the first laser light along the first direction.

20 Claims, 10 Drawing Sheets

MULTI-WAVELENGTH LASER DEVICE FOR PHOTOCOAGULATION SURGERY

CROSS-REFERENCE TO RELATED APPLICATION AND CLAIM OF PRIORITY

The application claims the benefit of Taiwan Patent Application No. 111137597, filed on Oct. 3, 2022, at the Taiwan Intellectual Property Office, the disclosures of which are incorporated herein in its entirety by reference.

FIELD OF THE INVENTION

The present invention is related to a multi-wavelength laser, and more particularly to a multi-wavelength laser apparatus for use during a photocoagulation surgery.

BACKGROUND OF THE INVENTION

Laser lights with light wavelength in the range of visible lights (about 360-830 nanometers) have high practical value, and the use of which is also appearing in industrial processing as well as in the application of medical technology. In the past decade, increased attention was paid to laser photocoagulation surgery in the art. Laser photocoagulation therapy is currently broadly used in the microsurgery for tissues near the retina or iris of the eyeball, which uses laser lights with energy level of watts as a tool, and selects laser light with a specific wavelength to perform the operation according to different locations of the eyeball. Currently there are four visible lasers suitable for photocoagulation. The wavelengths of the four lasers used in photocoagulation surgery are about 532, 577, 670 and 810 nanometers. Optical fibers are used to guide the laser lights toward the desired projection site, according to the technology known to the art.

When performing surgery, the physician needs to select a laser beam with an appropriate wavelength. He/she first uses the optical fiber to project a low-power red aiming light with a wavelength of about 635 nanometers to the affected area to determine the ideal location where the surgical laser beam will be projected, and then turns on the selected laser light for surgery. However, there is no device currently available on the market that allows the physician to easily switch among the above-mentioned four laser lights with different wavelengths while maintaining the projection of the red aiming light in the same optical path for guiding. Thus, when performing the operation, physicians often need to change equipment in order to target different portions of the eyeball, which limits the convenience of using the equipment during the operation.

Therefore, there is a need for a projection light source that can provide an optical fiber carrying visible light including laser lights with different wavelengths that may be used in the above-mentioned laser photocoagulation operation to solve the technical problems of the prior art.

SUMMARY OF THE INVENTION

The present invention provides a laser light source with multiple wavelengths to be used in laser photocoagulation operation. The novel technology can efficiently overcome the deficiencies of the prior art and provide a variety of visible laser lights with output power level of watts as required by the photocoagulation operation.

In accordance with one aspect of the present invention, a laser device for photocoagulation surgery is provided, wherein the laser device includes a multi-wavelength laser source having a first direction and a second direction different from the first direction. The laser device includes a positioning light source, a first laser light source, a first lens, a second laser light source, a second lens, a third laser light source, a third lens, a fourth laser light source and a fourth lens. The positioning light source configured to project a positioning visible light along the first direction, wherein the positioning visible light has a specific wavelength being about 635 nm. The first laser light source configured to project a first laser light having a first wavelength along the second direction. The first lens disposed in a main optical path of the positioning visible light, and configured to receive the first laser light and reflect the first laser light along the first direction. The second laser light source configured to project a second laser light having a second wavelength along the second direction. The second lens disposed in the main optical path, and configured to receive the second laser light and reflect the second laser light along the first direction. The third laser light source configured to project a third laser light having a third wavelength along the second direction. The third lens disposed in the main optical path, and configured to receive the third laser light and reflect the third laser light along the first direction. The fourth laser light source configured to project a fourth laser light having a fourth wavelength along the second direction. The fourth lens disposed in the main optical path, and configured to receive the fourth laser light and reflect the fourth laser light along the first direction. The first wavelength is longer than the second wavelength, the second wavelength is longer than the specific wavelength, the specific wavelength is longer than the third wavelength, the third wavelength is larger than the fourth wavelength, and each of the first, the second, the third and the fourth wavelengths is within a visible light waveband; the first lens has a first high transmittance for a first waveband including any wavelength shorter than the first wavelength. The second lens has a second high transmittance for a second waveband including any wavelength shorter than the second wavelength; the third lens has a third high transmittance for a third waveband including any wavelength longer than the third wavelength. The fourth lens has a fourth high transmittance for a fourth waveband including any wavelength longer than the fourth wavelength. The first lens is disposed near the second lens, and is placed downstream of the second lens in the main optical path. The third lens is disposed near the fourth lens, and is placed upstream of the fourth lens in the main optical path.

In accordance with another aspect of the present invention, a multi-wavelength laser device having a first direction and a second direction different from the first direction is provided. The multi-wavelength laser device includes a positioning light source configured to project a positioning visible light along the first direction, wherein the positioning visible light has a specific wavelength; a first laser light source configured to project a first laser light having a first wavelength along the second direction; a first lens disposed in a main optical path of the positioning visible light, and configured to receive the first laser light and reflect the first laser light along the first direction; a second laser light source configured to project a second laser light having a second wavelength along the second direction; a second lens disposed in the main optical path, and configured to receive the second laser light and reflect the second laser light along the first direction; a third laser light source configured to project a third laser light having a third wavelength along the second direction; a third lens disposed in the main optical path, and configured to receive the third laser light and reflect the third laser light along the first direction; a fourth laser light source configured to project a fourth laser light having a fourth wavelength along the second direction; and a fourth lens disposed in the main optical path, and configured to receive the fourth laser light and reflect the fourth laser light along the first direction, wherein the first wavelength is longer than the second wavelength, the second wavelength is longer than the specific wavelength, the specific wavelength is longer than the third wavelength, and the third wavelength is larger than the fourth wavelength; the first lens has a first high transmittance for a first waveband including any wavelength shorter than the first wavelength; the second lens has a second high transmittance for a second waveband including any wavelength shorter than the second wavelength; the third lens has a third high transmittance for a third waveband including any wavelength longer than the third wavelength; the fourth lens has a fourth high transmittance for a fourth waveband including any wavelength longer than the fourth wavelength; the first lens is disposed near the second lens, and is placed at a downstream location with respect to the second lens in the main optical path; and the third lens is disposed near the fourth lens, and is placed at an upstream location with respect to the fourth lens in the main optical path.

The high-power laser provided by the present invention is applicable for the use of medical surgery or industrial manufacturing, so it has industrial utilization.

The objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Figure 1:
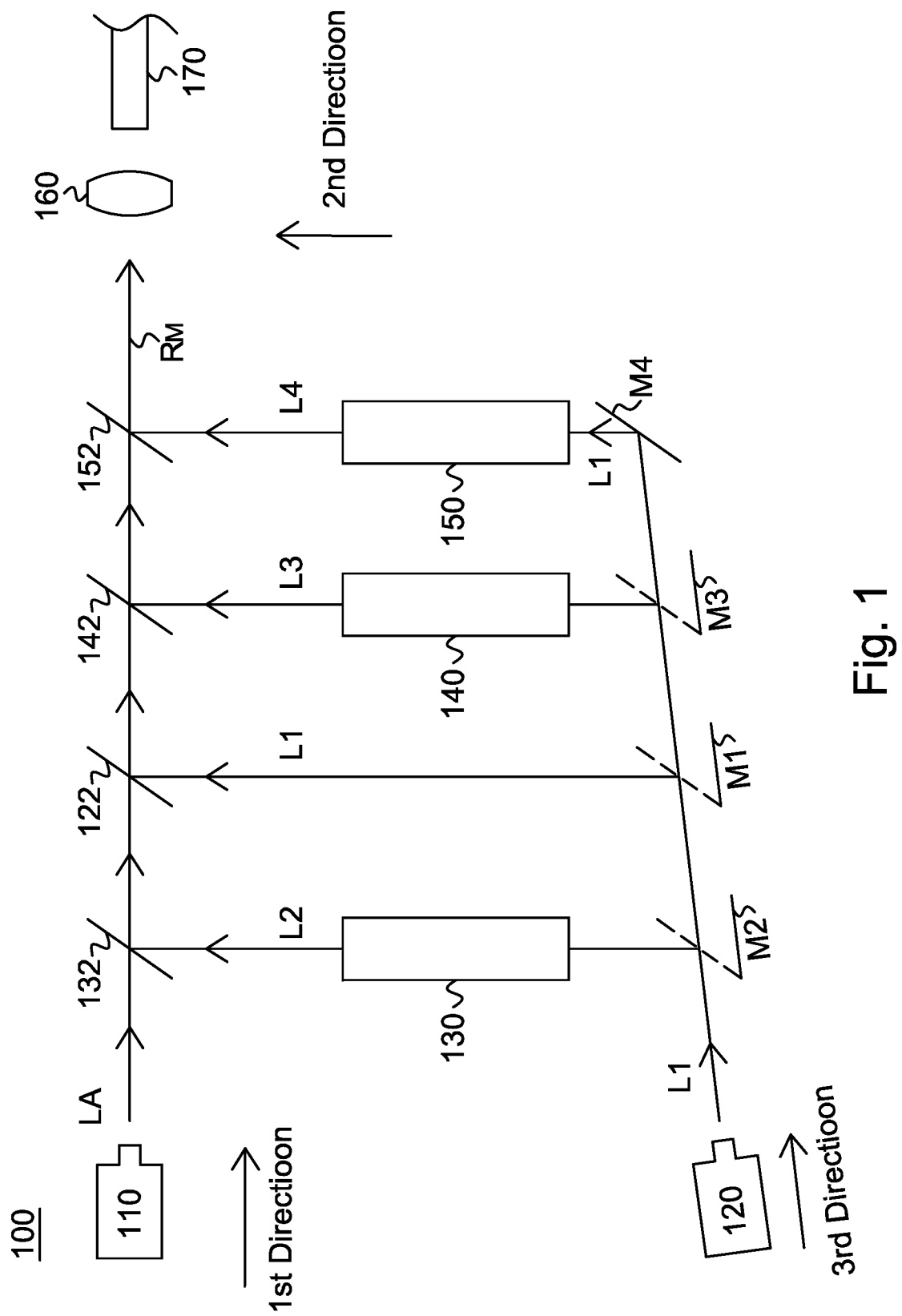
FIG. 1 is a schematic diagram showing a multi-wavelength laser device for generating visible laser lights according to one embodiment of the present invention.

Please refer to FIG. 1, which shows a schematic diagram of an embodiment of a visible light multi-wavelength laser device according to the present invention. As shown in the figure, the multi-wavelength laser device 100 has a first direction, a second direction and a third direction indicated by arrows. The first direction is different from the second direction, and the user can arrange the angular relationship between the two according to different designs. The angle between the two can be close to vertical which is 90 degrees, or any other angle such as 45, 60 and 75 degrees.

The laser device 100 has a positioning light source 110, which is configured to inject the positioning visible light LA with a specific wavelength of about 635 nm along the first direction, and the projection path of the positioning visible light LA forms a main optical path of the laser device 100. The selection of this specific wavelength is based on the consideration of the 635 nm red light commonly used by laser devices currently providing photocoagulation surgery, which may constitute a clear difference with the visible laser light of 4 different wavelengths employed in the photocoagulation surgery, so as to provide easy color discrimination during operation on one hand and possess cost advantage due to this light source on the other hand.

As shown in the figure, the laser device 100 includes a first laser light source 120, a second laser light source 130, a third laser light source 140, and a fourth laser light source 150, which are configured to project a first laser light L1 with the first wavelength, a second laser light L2 with a second wavelength, a third laser light L3 with a third wavelength, and a fourth laser light L4 with a fourth wavelength along the second direction respectively. The first wavelength is greater than the second wavelength, the second wavelength is greater than the specific wavelength, the specific wavelength is greater than the third wavelength, and the third wavelength is greater than the fourth wavelength. According to the requirements of photocoagulation surgery, the first, the second, the third and the fourth wavelengths are all in the visible light band (about 390-700 nanometers). However, the present invention can also be applied to wavelengths falling in the infrared or ultraviolet light band range.

According to an embodiment, the second laser light source 130, the third laser light source 140 and the fourth laser light source 150 can all be derived from the first laser light source 120. As shown in FIG. 1, the first laser light source 120 provides the first laser light L1 along the third direction, and the laser device 100 is equipped with a first mirror M1, a second mirror M2, a third mirror M3, and a fourth mirror M4 along the path of the third direction, wherein the first three can be located in different positions under the control of the user, as shown by the dotted line, such a combination can selectively reflect the first laser light L1 from the third direction to the second direction, and then be projected to the optical devices that need to pass therethrough. For example, the second laser light source 130 receives the first laser light L1 from the first laser light source 120, converts the first laser light L1 into the second laser light L2, and then have the second laser light L2 projected along the second direction.

According to other embodiments, anyone of the second laser light source 130, the third laser light source 140 and the fourth laser light source 150 can be a single light source rather than the one originated from the first laser light source 120.

Since the first direction is different from the second direction, it is necessary to configure optical elements at appropriate positions along the main optical path to reflect laser light of various wavelengths to the first direction, so that the incident laser light and positioning visible light LA may travel virtually along the same path, and thus the positioning visible light LA can provide the operator with the use of positioning.

These optical elements include a first lens 122, a second lens 132, a third lens 142 and a fourth lens 152, configured to respectively receive the first, second, third and fourth laser lights L1-L4 according to the angular relationship between the first direction and the second direction and reflect these laser lights along the first direction. In this embodiment, the arrangement sequence from upstream to downstream is the second lens 132, the first lens 122, the third lens 142 and the fourth lens 152 on the main optical path of the projection path of the positioning visible light LA.

At the relatively downstream position of the main optical path, the multi-wavelength laser device 100 is equipped with a focusing lens 160 configured to be incident to the laser light from the main optical path and the positioning visible light LA towards the output optical fiber 170, so as to provide the user with photocoagulation or other operations that require multiple wavelengths of laser light.

Notably, in order to effectively reflect the light that needs to be reflected fully, and to allow the light propagating along the main optical path to penetrate the optical elements on the main optical path with minimal loss, the characteristics of these lenses 122-152 and the positions of the lenses 122-152 arranged on the main optical path need to be properly determined. Generally, the reflectivity or transmittance of the commonly used semi-lens is far lower than 80%, which results in too much loss in laser power and cannot meet the requirements of the laser device used for photocoagulation surgery of the present invention.

Please refer to FIGS. 4-7, which show the transmittance of each lens arranged in the main optical path of the visible light multi-wavelength laser device of the present invention for lights of different wavelengths. According to an embodiment of the present invention, in order to meet the needs of photocoagulation surgery. The first wavelength is about 810 nanometers, which can be realized by using a laser light source with a wavelength of about 808 nanometers in practical application. The second wavelength is about 670 nanometers which can be realized by using a laser light source with a wavelength of about 670 nanometers in practical application. The third wavelength is about 577 nanometers, which can be realized by using a laser light source with a wavelength of about 579 nanometers in practice. The fourth wavelength is about 532 nanometers, which can be realized by using a laser light source with a wavelength of about 532 nanometers.

Figure 4:
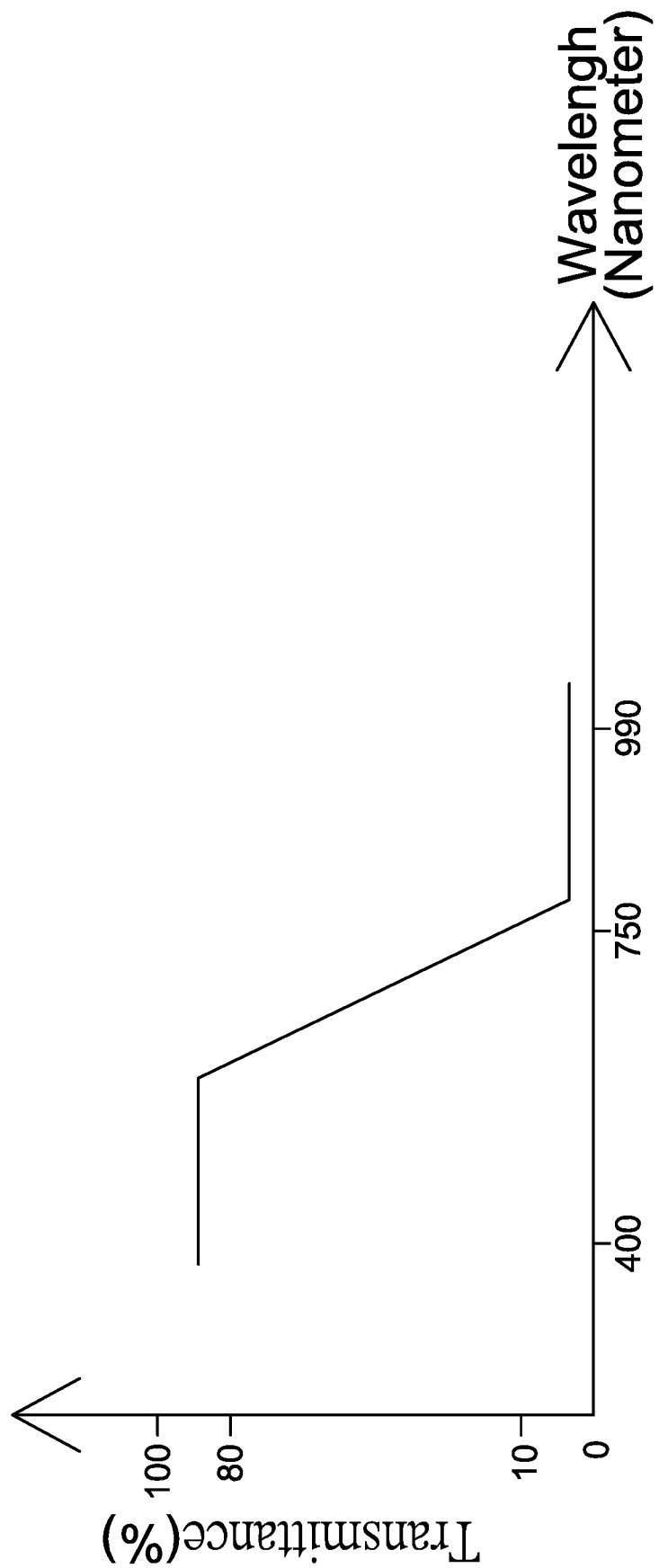
FIGS. 4-7 are schematic diagrams showing the transmittance of each lens arranged in the main optical path of the visible light multi-wavelength laser device of the present invention for lights of different wavelengths.

FIG. 4 shows that the first lens 122 is a short-pass filter element, which has a transmittance higher than 80% for the lights whose wavelength falls within the first waveband near or less than 725 nanometers, preferably the transmittance is greater than 85% or even higher, and a high reflectivity for the lights with the first wavelength, i.e., a wavelength of about 808 nanometers or greater. The transmittance shown in the figure is far less than 10%, preferably less than 5%, for light with a wavelength of about 800-990 nanometers. As a result, the laser light with a wavelength of about 808 nanometers can be reflected from the second direction to the first direction and projected along the main optical path, while other lights with relatively shorter wavelengths employed in this embodiment can penetrate through with low power loss.

Figure 5:
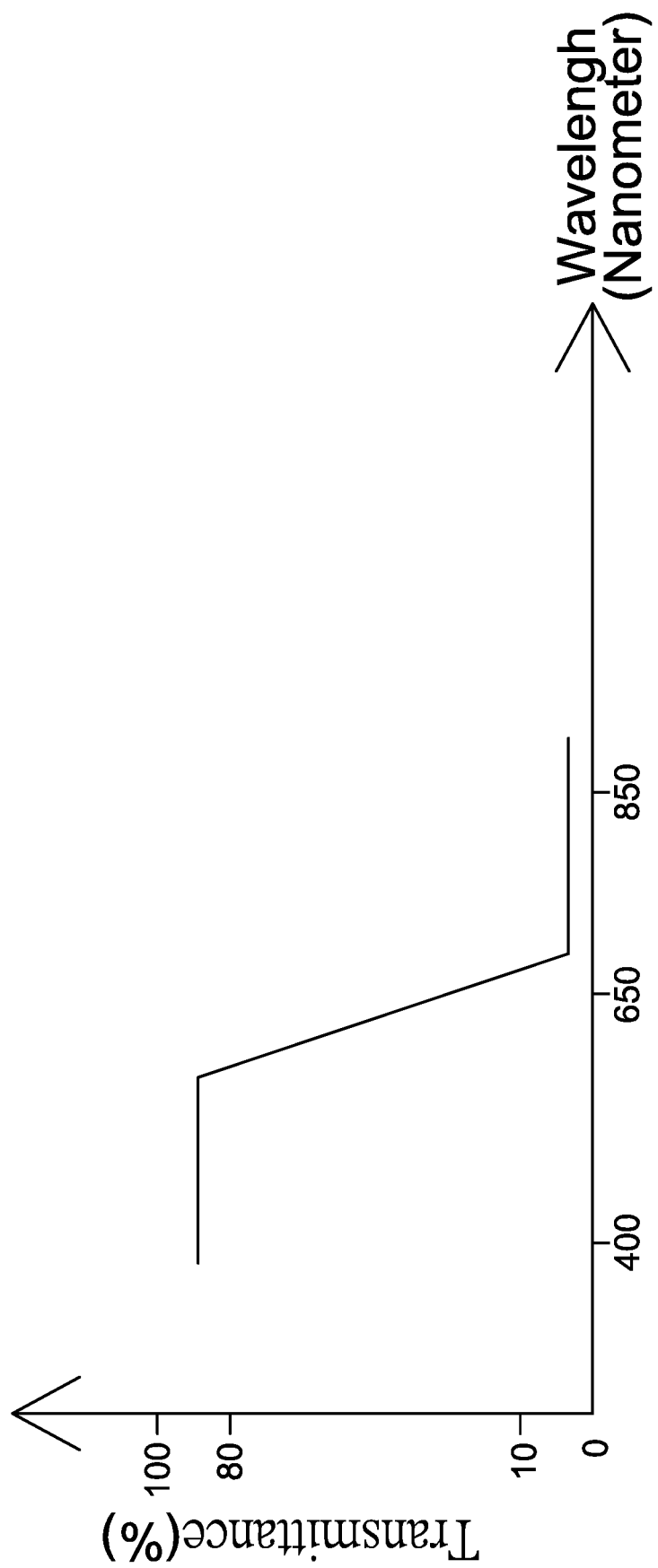

FIG. 5 shows that the second lens 132 is a short-pass filter element, which has a transmittance higher than 80% for the lights whose wavelength falls within the second waveband near or less than 630 nanometers, preferably the transmittance is greater than 85% or even higher, and a high reflectivity for the lights with the second wavelength, i.e., a wavelength of about 670 nanometers or greater. The transmittance shown in the figure is far less than 10%, preferably less than 5%, for light with a wavelength of about 675-850 nanometers. As a result, the laser light with a wavelength of about 670 nanometers can be reflected from the second direction to the first direction and projected along the main optical path, while other lights with relatively shorter wavelengths employed in this embodiment can penetrate through with low power loss.

Figure 6:
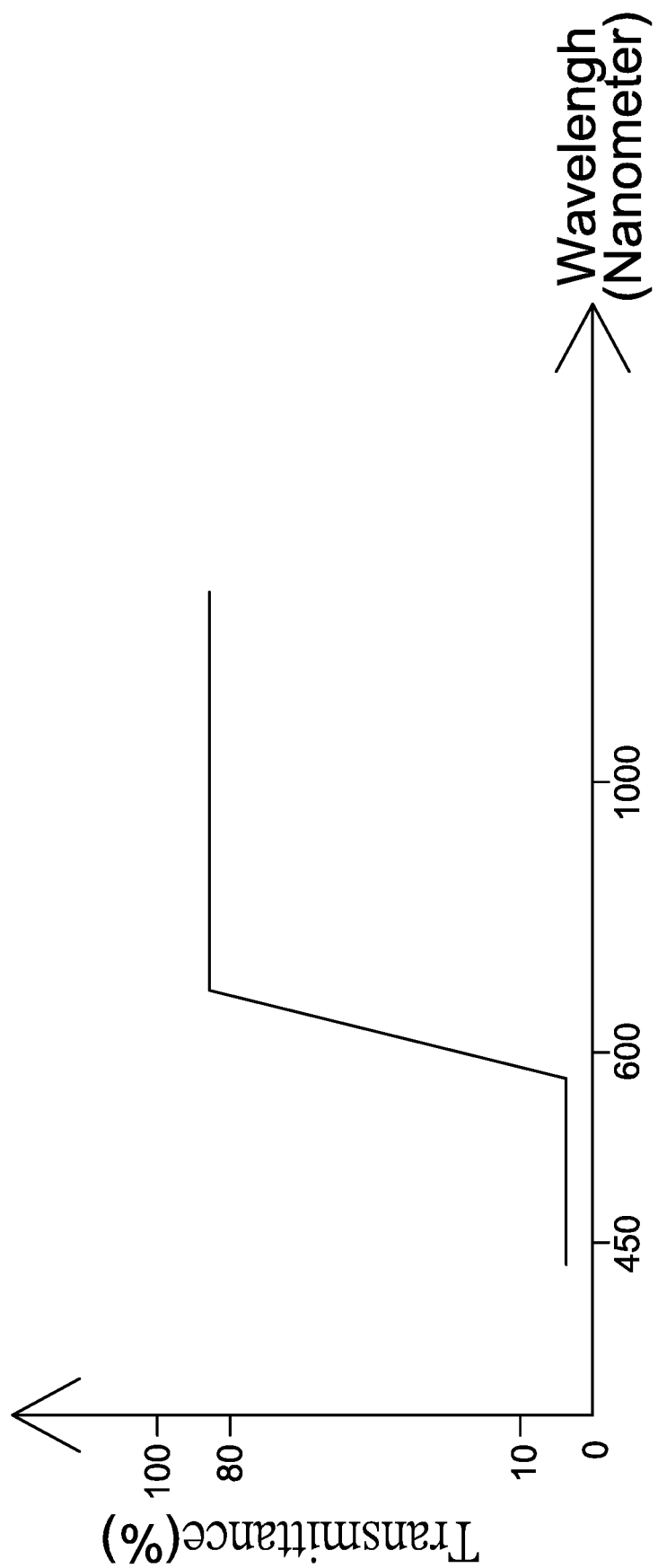

FIG. 6 shows that the third lens 142 is a long-pass filter element, which has a transmittance higher than 80% for the lights whose wavelength falls within the third waveband near or greater than 625 nanometers, preferably the transmittance is greater than 85% or even higher, and a high reflectivity for the lights with the third wavelength, i.e., a wavelength of about 577 nanometers or less. The transmittance shown in the figure is far less than 10%, preferably less than 5%, for light with a wavelength of about 460-570 nanometers. As a result, the laser light with a wavelength of about 577 nanometers can be reflected from the second direction to the first direction and projected along the main optical path, while other lights with relatively shorter wavelengths employed in this embodiment can penetrate through with low power loss.

Figure 7:
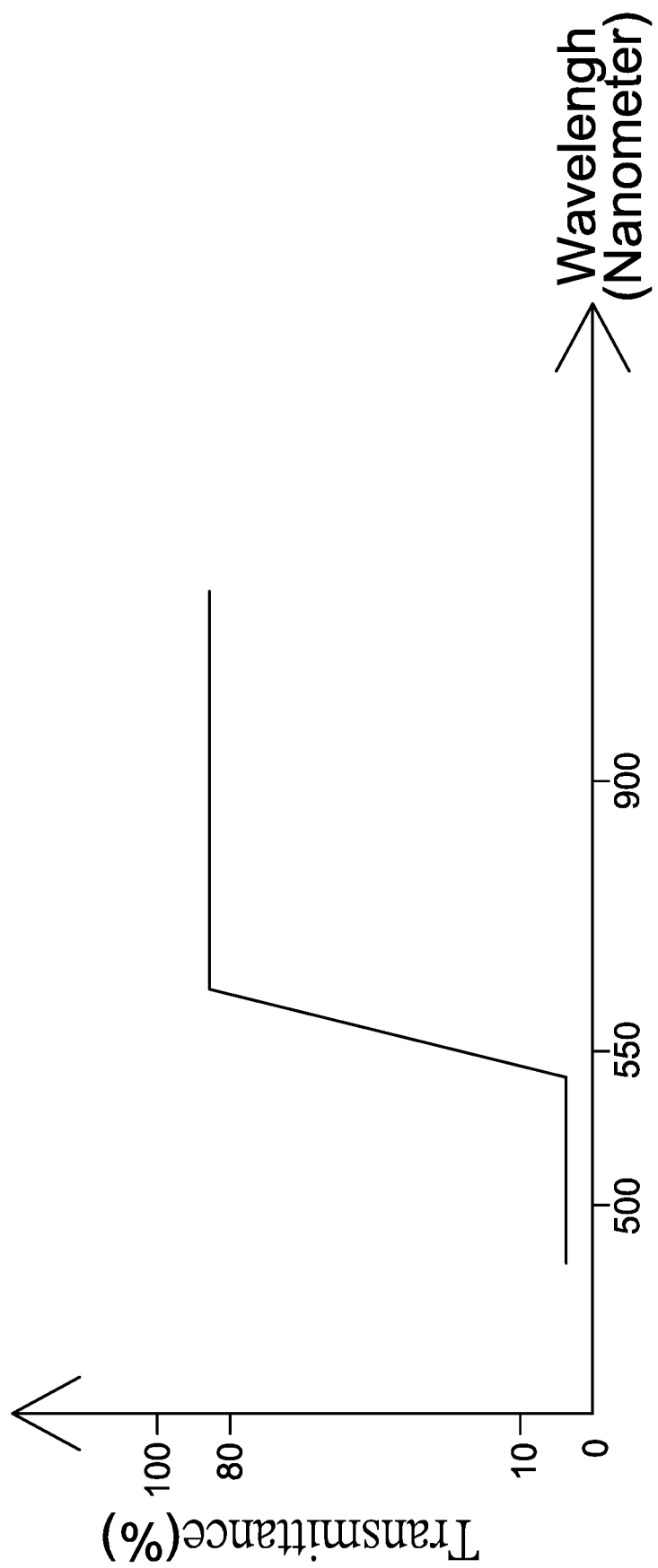

FIG. 7 shows that the fourth lens 152 is a long-pass filter element, which has a transmittance higher than 80% for the lights whose wavelength falls within the third waveband near or greater than 550 nanometers, preferably the transmittance is greater than 85% or even higher, and a high reflectivity for the lights with the fourth wavelength, i.e., a wavelength of about 532 nanometers or less. The transmittance shown in the figure is far less than 10%, preferably less than 5%, for light with a wavelength of about 450-535 nanometers. As a result, the laser light with a wavelength of about 532 nanometers can be reflected from the second direction to the first direction and projected along the main optical path, while other lights with relatively shorter wavelengths employed in this embodiment can penetrate through with low power loss.

Notably, the filtering properties of the lenses 122-152 shown in FIGS. 4-7 are exemplary embodiments for the wavelength of the incident light. Those skilled persons in the art may choose appropriate lens filtering specifications based on the consideration of the actual laser wavelength or material cost. The lenses 122-152 used in the present invention are either long-pass or short-pass filter elements with simple specifications. Through proper configuration, the production cost can be effectively reduced while achieving the desired effect.

Figure 2:
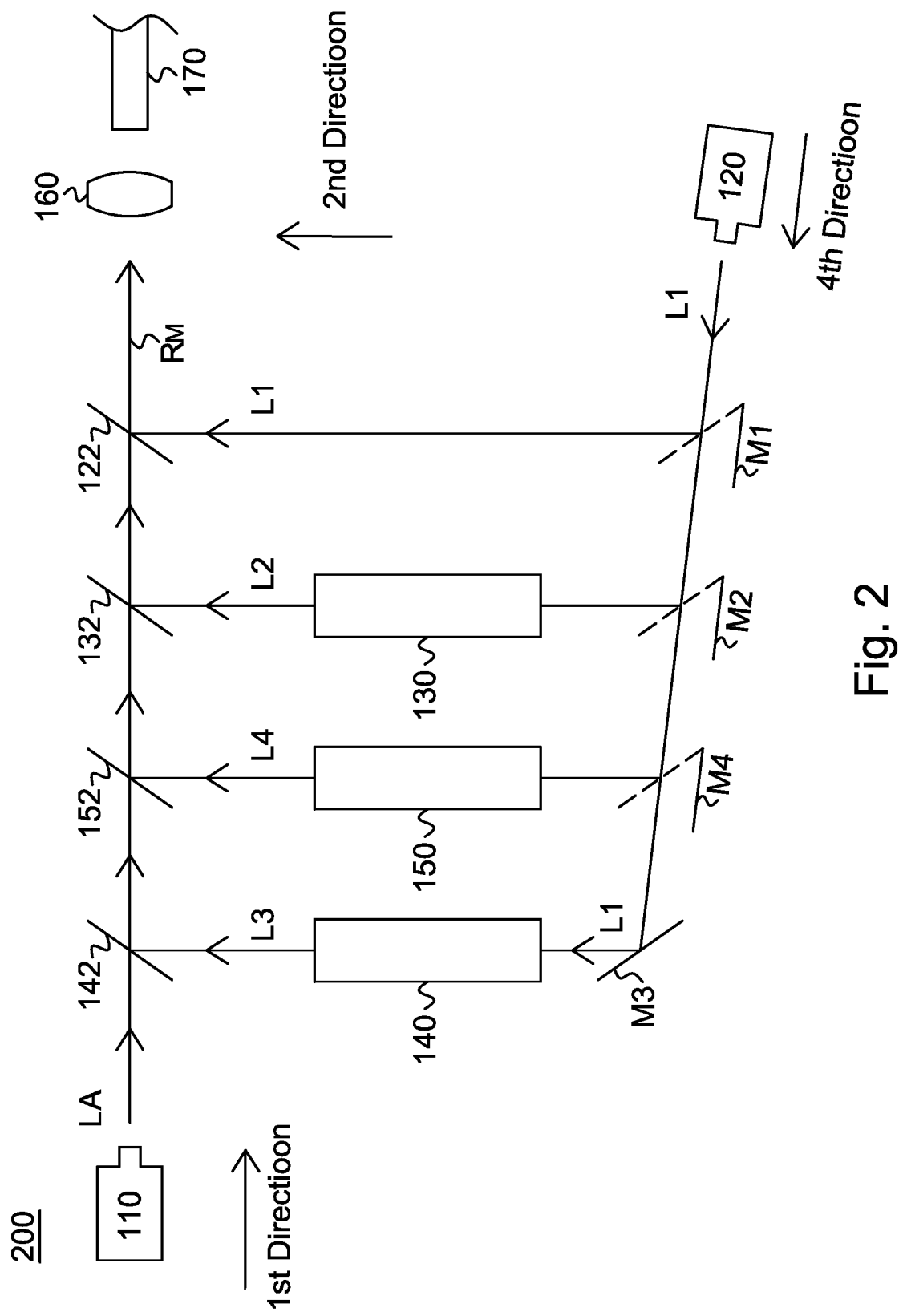
FIG. 2 is a schematic diagram of a multi-wavelength laser device for generating visible laser lights according to another embodiment of the present invention.

Please refer to FIG. 2, which shows a schematic diagram of a multi-wavelength laser device for generating visible laser lights according to another embodiment of the present invention. As shown in the figure, the multi-wavelength laser device 200 has a first direction, a second direction and a fourth direction indicated by arrows. The optical elements in this embodiment are virtually the same with those illustrated in FIG. 1, and thus there is no need to repeat.

In FIG. 2, except that the first laser light source 120 projects the first laser light L1 along the fourth direction, the four lenses are disposed on the main optical path where the positioning visible light LA are projected therethrough, following the arrangement sequence from upstream to downstream: the third lens 142, the fourth lens 152, the second lens 132 and the first lens 122. In addition, the first mirror M1, the second mirror M2, the third mirror M3 and the fourth mirror M4 configured to project the first laser light L1 form the first laser light source 120 to the second direction are disposed according to the devices or the optical path arrangement shown in FIG. 2, which is different from the arrangement sequence in the embodiment shown in FIG. 1.

To sum up, the light of various wavelengths, including the positioning visible light LA and the first, second, third and fourth laser light L1, L2, L3, L4, each of which can travel through the predetermined optical path, eventually enters the focusing lens 160 along the main optical path and is incident towards the output optical fiber 170, when necessary. Along the main optical path, the first lens 122 needs to be configured adjacent to the second lens 132, and should be at a downstream position relative to the second lens 132, while the third lens 142 needs to be arranged adjacent to the fourth lens 152, and should be at an upstream position relative to the fourth lens 152.

Taking FIG. 1 as an example, the short-pass filter element of the first lens 122 has high transmittance for lights whose wavelength fall within the first waveband, and has high reflectivity for lights having the first wavelength L1. When the first lens 122 is disposed downstream of the second lens 132, it can allow the positioning visible light LA and the second laser light L2 with a shorter wavelength to pass through, while letting the first laser light L1 with a longer wavelength to be reflected into the main optical path. In the embodiment of FIG. 2, the first lens 122 is arranged at the most downstream position of the main optical path, allowing the second, the third and the fourth laser light L2, L3, L4 and the positioning visible light LA with a shorter wavelength to pass through, while the first laser light L1 with a longer wavelength can be reflected into the main optical path.

Likewise, the long-pass filter element of the fourth lens 152 has high transmittance for lights whose wavelength fall within the fourth waveband, and has high reflectivity for lights having the fourth wavelength L4. When the third lens 142 is disposed upstream of the fourth lens 152, in other words, the fourth lens 152 is arranged downstream of the third lens 142, taking FIG. 1 for instance, the first, the second and the third laser lights L1, L2, L3 and the positioning visible light LA with longer wavelength can penetrate therethrough, while allowing the fourth laser light L4 with a shorter wavelength to be reflected into the main optical path.

Comparing the arrangement of FIG. 1 with that of FIG. 2, it can be understood that according to the concept of the present invention, the first lens 122 and the second lens 132 categorized into the short-pass filter elements need to be arranged adjacently, while the third lens 142 and the fourth lens 152 categorized into the long-pass filter elements also need to be arranged adjacently. If one considers that the third and the second laser light L3, L4 with shorter wavelengths may reduce the energy loss due to penetrating optical elements, the configuration in FIG. 1 can be selected.

Figure 3:
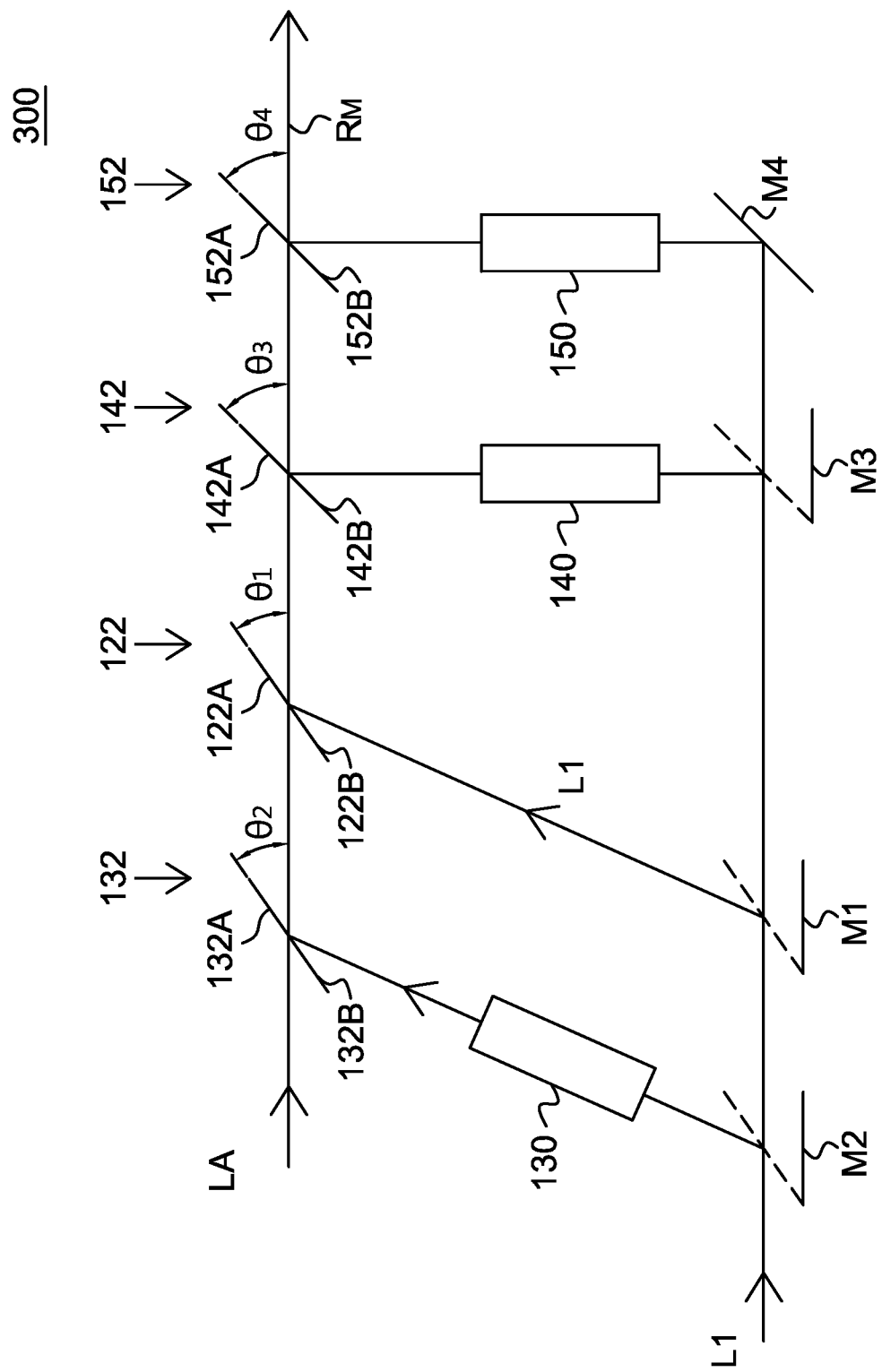
FIG. 3 is a schematic diagram of a multi-wavelength laser device for generating visible laser lights according to yet another embodiment of the present invention.

Please refer to FIG. 3, which shows a schematic diagram of another embodiment of a multi-wavelength laser device for generating visible laser lights according to the present invention. As shown in the figure, the properties of the components in the multi-wavelength laser device 300 are similar to those in FIG. 1, so there is no need to repeat.

FIG. 3 differs from FIG. 1 in that the first, the second, third and the fourth laser light L1, L2, L3, L4 in the multi-wavelength laser device 300 are not limited to be projected to the first, the second, the third and the fourth lens 122, 132, 142,152 with the same projection angle, but utilize the first, the second, the third and the fourth angles θ1, θ2, θ3, θ4 respectively formed between the first, the second, the third and the fourth lens 122, 132, 142,152 and the main optical path to allow the first, the second, the third and the fourth laser lights L1, L2, L3, L4 to be projected onto the main optical path. In addition, the first, the second, the third and the fourth lens 122, 132, 142,152 each has a first surface 122A, 132A, 142A, 152A facing the incident direction of the visible light LA and an opposite second surface 122B, 132B, 142B, 152B. In order to achieve the optical properties required by the first, the second, the third and the fourth lens 122, 132, 142,152, one of the surfaces of each lens can be selected to be coated with a suitable optical film.

In the abovementioned embodiments, the second laser light source 130, the third laser light source 140 and the fourth laser light source 150 can be separate laser light sources, or can be obtained by changing the transmission frequency of the first laser light L1 with different means for generating the second, the third and the fourth laser lights L2, L3, L4 respectively. The following are some examples of laser cavities based on the concept of solid-state Physics. The skilled persons in the art may use different laser devices as appropriate.

Figure 8:
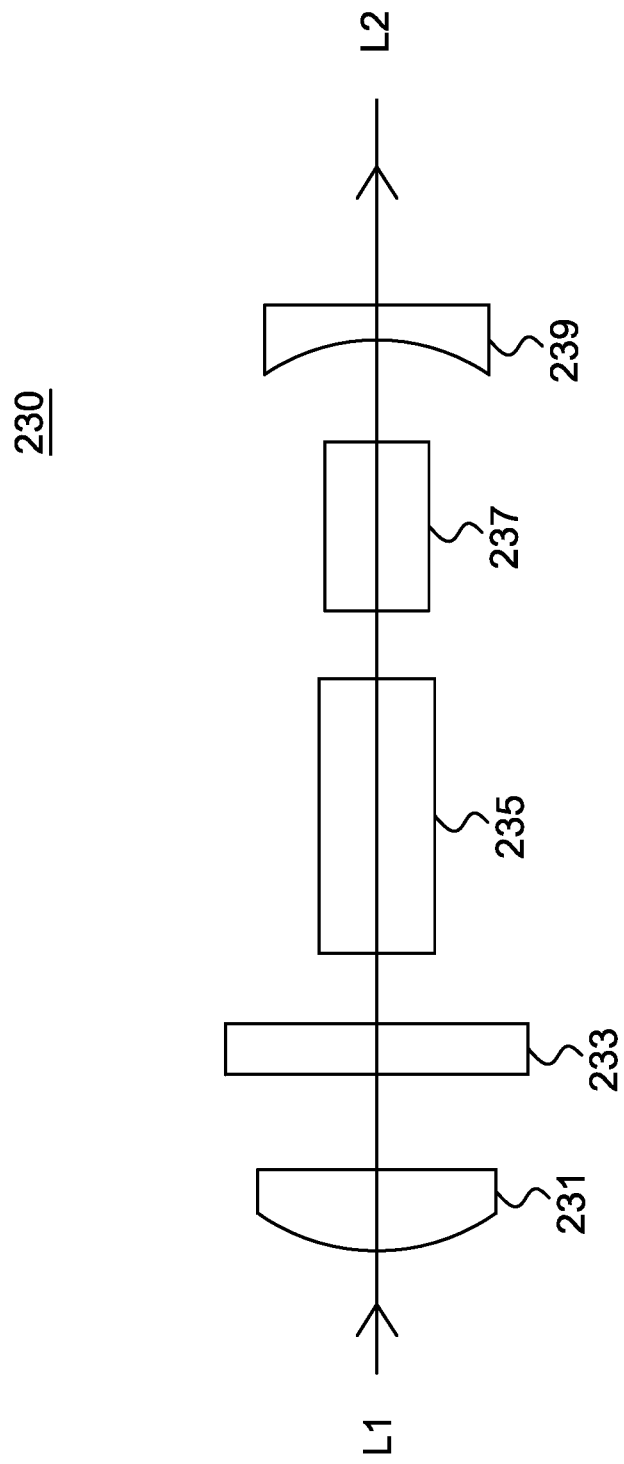
FIG. 8 shows a schematic diagram of the laser device for generating laser light with a wavelength of 670 nanometers according to an embodiment of the present invention.

FIG. 8 shows a linear resonant cavity 230 that converts the first laser light L1 into the second laser light L2, and is configured with an incident lens 231, a functional lens 233, gain and Raman medium 235, a frequency-doubling crystal 237 and output mirror 239, along the incident direction of the first laser light L1. The gain and Raman medium 235 includes neodymium-doped vanadate (such as neodymium-doped yttrium vanadate Nd: YVO4), which can absorb the first laser light L1 with a wavelength of about 808 nm and generate a laser light (not shown) with wavelength of about 1342 nm. The frequency-doubling crystal 237 is a lithium triborate (LBO) crystal formed with a special cutting angle, which can double the laser light frequency of 1342 nanometers to produce a laser light with a wavelength of about 671 nanometers (not shown). A standing wave is formed between the functional lens 233 and the output mirror 239 by the produced laser with wavelength of about 671 nanometers, and finally outputs as the second laser light L2.

Figure 9:
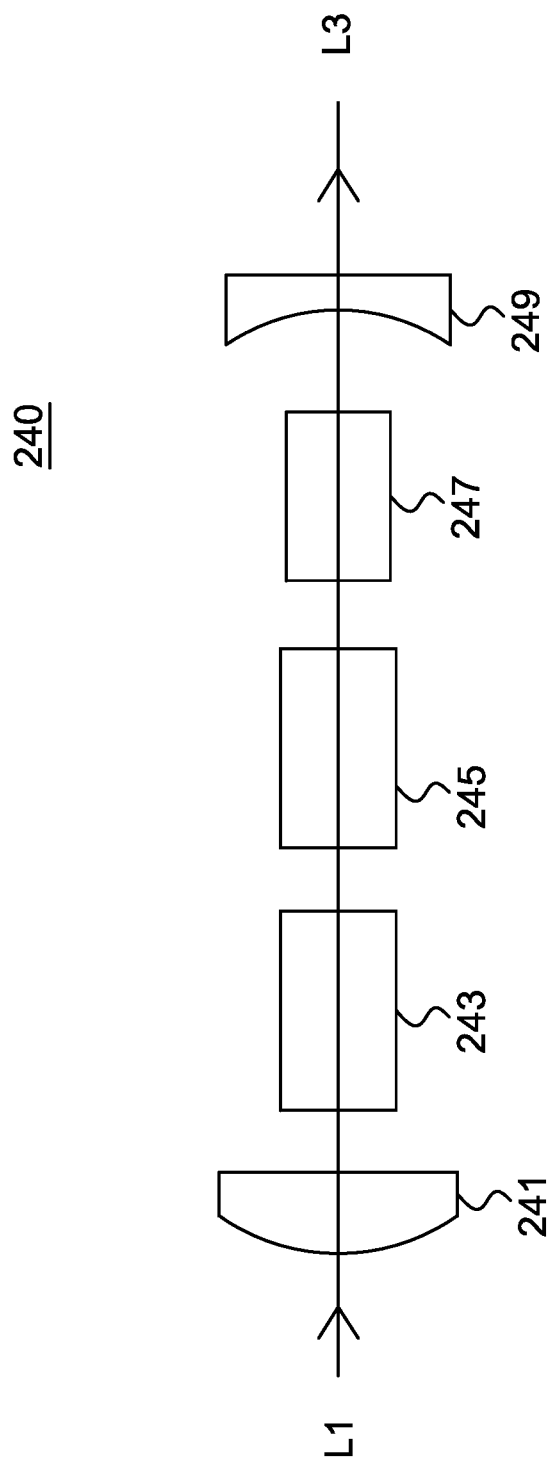
FIG. 9 shows a schematic diagram of the laser device for generating laser light with a wavelength of 579 nanometers according to an embodiment of the present invention.

FIG. 9 shows a linear resonant cavity 240 that converts the first laser light L1 into the third laser light L3, and is configured with an incident lens 241, a gain medium 243, and a Raman medium 245, nonlinear crystal 247 and output mirror 249 along the incident direction of the first laser light L1. The gain medium 243 comprises vanadate doped with neodymium. The Raman medium 245 comprises ytterbium-doped potassium gadolinium tungstate crystal (KGW). The nonlinear crystal 247 is another kind of LBO crystal. The linear resonant cavity 240 receives first laser light L1, and eventually the third laser light L3 with a wavelength of about 579 nm is output. According to another embodiment, the gain medium 243 may be a yttrium aluminum garnet (Nd: YAG) crystal doped with neodymium, and the Raman medium 245 contains neodymium-doped vanadate (such as neodymium-doped yttrium vanadate Nd:YVO4).

Figure 10:
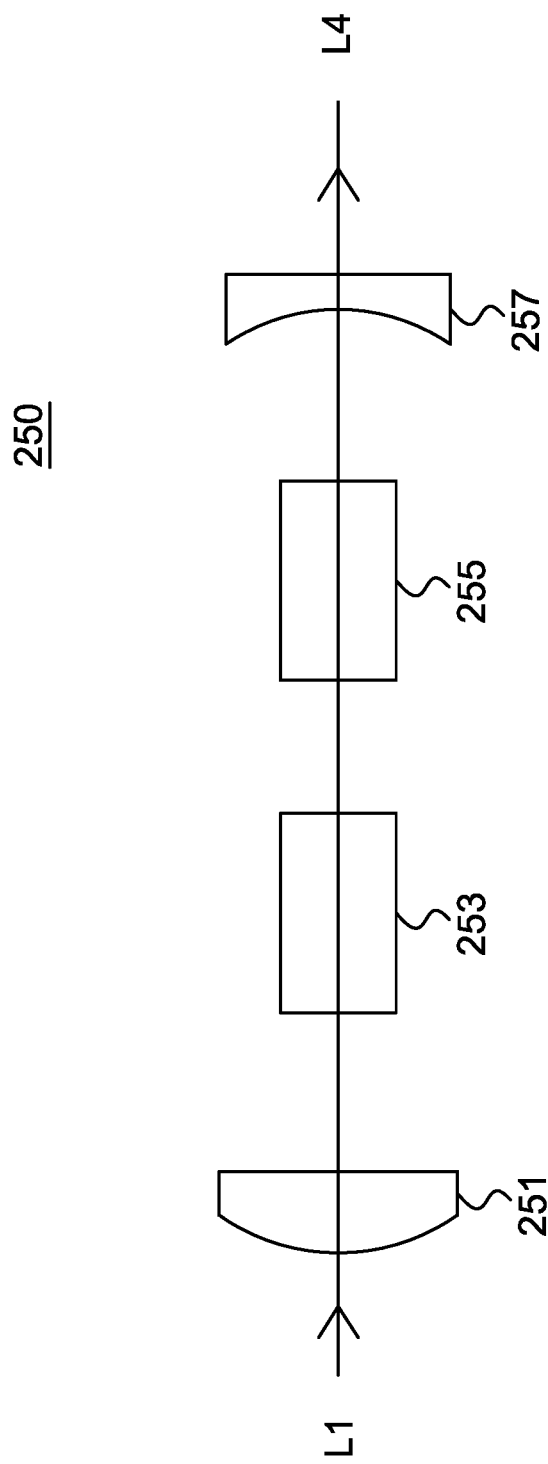
FIG. 10 shows a schematic diagram of the laser device for generating laser light with a wavelength of 532 nanometers according to an embodiment of the present invention.

FIG. 10 shows a linear resonant cavity 250 that converts the first laser light L1 into the fourth laser light L4, and is configured with an incident lens 251, a gain medium 253, a frequency-doubling crystal 255 and output mirror 257 along the incident direction of the first laser light L1. The gain medium 253 contains neodymium-doped vanadate, and the frequency-doubling crystal 255 can be a nonlinear crystal containing potassium titanyl phosphate (KTP), or a lithium triborate (LBO) crystal formed at a special cutting angle. In the linear resonator 250, the first laser light L1 with a wavelength of about 808 nm is received, and the fourth laser light L4 with a wavelength of about 532 nm is eventually output.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A laser device for photocoagulation surgery, wherein the laser device includes a multi-wavelength laser source having a first direction and a second direction different from the first direction, comprising:
    a positioning light source configured to project a positioning visible light along the first direction, wherein the positioning visible light has a specific wavelength being about 635 nm;
    a first laser light source configured to project a first laser light having a first wavelength along the second direction;
    a first lens disposed in a main optical path of the positioning visible light, and configured to receive the first laser light and reflect the first laser light along the first direction;
    a second laser light source configured to project a second laser light having a second wavelength along the second direction;
    a second lens disposed in the main optical path, and configured to receive the second laser light and reflect the second laser light along the first direction;
    a third laser light source configured to project a third laser light having a third wavelength along the second direction;
    a third lens disposed in the main optical path, and configured to receive the third laser light and reflect the third laser light along the first direction;
    a fourth laser light source configured to project a fourth laser light having a fourth wavelength along the second direction; and
    a fourth lens disposed in the main optical path, and configured to receive the fourth laser light and reflect the fourth laser light along the first direction, wherein:
    the first wavelength is longer than the second wavelength, the second wavelength is longer than the specific wavelength, the specific wavelength is longer than the third wavelength, the third wavelength is larger than the fourth wavelength, and each of the first, the second, the third and the fourth wavelengths is within a visible light waveband;
    the first lens has a first high transmittance for a first waveband including any wavelength shorter than the first wavelength;
    the second lens has a second high transmittance for a second waveband including any wavelength shorter than the second wavelength;
    the third lens has a third high transmittance for a third waveband including any wavelength longer than the third wavelength;
    the fourth lens has a fourth high transmittance for a fourth waveband including any wavelength longer than the fourth wavelength;
    the first lens is disposed near the second lens, and is placed downstream of the second lens in the main optical path; and
    the third lens is disposed near the fourth lens, and is placed upstream of the fourth lens in the main optical path.

2. The laser device according to claim 1, wherein the first laser light source includes a pumping light source providing the first laser light and a first mirror.

3. The laser device according to claim 2, wherein the first mirror is configured to project the first laser light along the second direction.

4. The laser device according to claim 1, further comprising a focusing lens disposed in the main optical path, and configured to receive the positioning visible light and at least one of the first, the second, the third and the fourth laser lights.

5. The laser device according to claim 4, further comprising an optical fiber configured to transmit any light received by the focusing lens.

6. The laser device according to claim 1, wherein the first lens has a first high reflectivity for a light having a wavelength no shorter than the first wavelength, and the second lens has a second high reflectivity for a light having a wavelength no shorter than the second wavelength.

7. The laser device according to claim 1, wherein the third lens has a third high reflectivity for a light having a wavelength no longer than the third wavelength, and the fourth lens has a fourth high reflectivity for a light having a wavelength no longer than the fourth wavelength.

8. The laser device according to claim 1, wherein the second laser light source includes a gain and Raman medium and a first doubling harmonic generation crystal, and is configured to receive the first laser light to generate the second laser light.

9. The laser device according to claim 1, wherein the third laser light source includes a first gain medium, a Raman medium and a non-linear crystal, and is configured to receive the first laser light to generate the third laser light.

10. The laser device according to claim 1, wherein the fourth laser light source includes a second gain medium and a second doubling harmonic generation crystal, and is configured to receive the first laser light to generate the fourth laser light.

11. A multi-wavelength laser device having a first direction and a second direction different from the first direction, and comprising:
    a positioning light source configured to project a positioning visible light along the first direction, wherein the positioning visible light has a specific wavelength;
    a first laser light source configured to project a first laser light having a first wavelength along the second direction;
    a first lens disposed in a main optical path of the positioning visible light, and configured to receive the first laser light and reflect the first laser light along the first direction;
    a second laser light source configured to project a second laser light having a second wavelength along the second direction;
    a second lens disposed in the main optical path, and configured to receive the second laser light and reflect the second laser light along the first direction;

a third laser light source configured to project a third laser light having a third wavelength along the second direction;

a third lens disposed in the main optical path, and configured to receive the third laser light and reflect the third laser light along the first direction;

a fourth laser light source configured to project a fourth laser light having a fourth wavelength along the second direction; and a fourth lens disposed in the main optical path, and configured to receive the fourth laser light and reflect the fourth laser light along the first direction, wherein:

the first wavelength is longer than the second wavelength, the second wavelength is longer than the specific wavelength, the specific wavelength is longer than the third wavelength, and the third wavelength is larger than the fourth wavelength;

the first lens has a first high transmittance for a first waveband including any wavelength shorter than the first wavelength;

the second lens has a second high transmittance for a second waveband including any wavelength shorter than the second wavelength;

the third lens has a third high transmittance for a third waveband including any wavelength longer than the third wavelength;

the fourth lens has a fourth high transmittance for a fourth waveband including any wavelength longer than the fourth wavelength;

the first lens is disposed near the second lens, and is placed at a downstream location with respect to the second lens in the main optical path; and the third lens is disposed near the fourth lens, and is placed at an upstream location with respect to the fourth lens in the main optical path.

12. The laser device according to claim 11, wherein the first laser light source includes a pumping light source providing the first laser light and a first mirror.

13. The laser device according to claim 12, wherein the first mirror is configured to project the first laser light along the second direction.

14. The laser device according to claim 11, wherein the specific wavelength is about 635 nm.

15. The laser device according to claim 11, wherein each of the first, the second, the third and the fourth wavelengths is within a visible light waveband.

16. The laser device according to claim 11, wherein the first lens has a first high reflectivity for a light having a wavelength no shorter than the first wavelength, and the second lens has a second high reflectivity for a light having a wavelength no shorter than the second wavelength.

17. The laser device according to claim 11, wherein the third lens has a third high reflectivity for a light having a wavelength no longer than the third wavelength, and the fourth lens has a fourth high reflectivity for a light having a wavelength no longer than the fourth wavelength.

18. The laser device according to claim 11, wherein the second laser light source includes a gain and Raman medium and a first doubling harmonic generation crystal, and is configured to receive the first laser light to generate the second laser light.

19. The laser device according to claim 11, wherein the third laser light source includes a first gain medium, a Raman medium and a non-linear crystal, and is configured to receive the first laser light to generate the third laser light.

20. The laser device according to claim 11, wherein the fourth laser light source includes a second gain medium and a second doubling harmonic generation crystal, and is configured to receive the first laser light to generate the fourth laser light.

* * * * *